United States Patent
Berthon-Jones et al.

(10) Patent No.: US 7,931,023 B2
(45) Date of Patent: Apr. 26, 2011

(54) PATIENT INTERFACE ASSEMBLY FOR CPAP RESPIRATORY APPARATUS

(75) Inventors: Michael Berthon-Jones, Leonay (AU); Michel Calluaud, Hunter's Hill (AU); Christopher Edward Lynch, Turramurra (AU); Colin Edward Sullivan, Birchgrove (AU)

(73) Assignee: ResMed Limited, Bella Vista, New South Wales (AU)

( * ) Notice: Subject to any disclaimer, the term of this patent is extended or adjusted under 35 U.S.C. 154(b) by 61 days.

(21) Appl. No.: 11/698,894

(22) Filed: Jan. 29, 2007

(65) Prior Publication Data

US 2007/0119454 A1    May 31, 2007

Related U.S. Application Data

(60) Continuation of application No. 10/385,701, filed on Mar. 12, 2003, now Pat. No. 7,302,950, which is a division of application No. 08/524,148, filed on Sep. 6, 1995, now abandoned, which is a continuation of application No. 07/994,153, filed on Dec. 21, 1992, now abandoned.

(30) Foreign Application Priority Data

Dec. 20, 1991 (AU) .................................. PL0148

(51) Int. Cl.
  *A61M 16/00* (2006.01)
  *A62B 7/00* (2006.01)
  *F16K 31/02* (2006.01)
(52) U.S. Cl. ............................. 128/204.21; 128/204.18
(58) Field of Classification Search ............. 128/200.24, 128/200.28, 201.22, 202.27, 203.12, 203.29, 128/204.11, 204.12, 205.25, 205.27, 206.12, 206.13, 206.14, 206.21, 206.27, 207.13, 207.18; 138/118, 119, 121

See application file for complete search history.

(56) References Cited

U.S. PATENT DOCUMENTS

| 853,431 | A | | 5/1907 | Allen | |
|---|---|---|---|---|---|
| 1,081,745 | A | * | 12/1913 | Johnston et al. | 128/203.25 |
| 1,176,886 | A | * | 3/1916 | Ermold | 128/207.13 |
| 1,632,449 | A | | 6/1927 | McKesson | |
| 2,007,440 | A | * | 7/1935 | Brand | 128/204.25 |
| 2,241,535 | A | * | 5/1941 | Boothby et al. | 128/205.17 |
| 2,245,969 | A | * | 6/1941 | Henry et al. | 128/207.18 |
| 2,931,358 | A | | 5/1960 | Sheridan | |
| 3,099,985 | A | | 8/1963 | Wilson et al. | |

(Continued)

FOREIGN PATENT DOCUMENTS

AU    A-62221/90    3/1991

(Continued)

OTHER PUBLICATIONS

International Application No. PCT/US90/02800 filed May 21, 1990.

(Continued)

*Primary Examiner* — Kristen C Matter
(74) *Attorney, Agent, or Firm* — Nixon & Vanderhye P.C.

(57) ABSTRACT

A patient interface assembly adapted to be connected to a gas supply pump to deliver pressurized breathable gas to the inlet of a patient's respiratory system includes a patient interface structured to provide a seal with the patient and at least one inlet tube provided to the patient interface. Each inlet tube includes a substantially flat lower side wall to face the patient and a substantially arcuate upper side wall.

61 Claims, 8 Drawing Sheets

U.S. PATENT DOCUMENTS

| | | | |
|---|---|---|---|
| 3,400,714 A | 9/1968 | Sheridan | |
| 3,502,100 A | 3/1970 | Jonson | |
| 3,513,844 A * | 5/1970 | Smith | 128/207.18 |
| 3,559,638 A | 2/1971 | Potter | |
| 3,720,235 A | 3/1973 | Schrock | |
| 3,726,270 A | 4/1973 | Griffis et al. | |
| 3,741,208 A | 6/1973 | Jonsson et al. | |
| 3,756,244 A | 9/1973 | Kinnear et al. | |
| 3,783,893 A | 1/1974 | Davison | |
| 3,802,431 A | 4/1974 | Farr | |
| 3,859,995 A | 1/1975 | Colston | |
| 3,865,106 A * | 2/1975 | Palush | 128/200.18 |
| 3,867,946 A | 2/1975 | Huddy | |
| 3,903,875 A | 9/1975 | Hughes | |
| 3,914,994 A | 10/1975 | Banner | |
| 3,932,054 A | 1/1976 | McKelvey | |
| 3,985,467 A | 10/1976 | Lefferson | |
| 3,992,598 A | 11/1976 | Welsh et al. | |
| 3,995,661 A | 12/1976 | Van Fossen | |
| 4,018,221 A | 4/1977 | Rennie | |
| 4,109,749 A | 8/1978 | Sweet | |
| 4,119,096 A | 10/1978 | Drews | |
| 4,206,754 A | 6/1980 | Cox et al. | |
| 4,249,527 A | 2/1981 | Ko et al. | |
| 4,257,422 A | 3/1981 | Duncan | |
| 4,301,833 A | 11/1981 | Donald, III | |
| 4,312,235 A | 1/1982 | Daigle | |
| 4,387,722 A | 6/1983 | Kearns | |
| 4,396,034 A | 8/1983 | Cherniak | |
| 4,406,283 A | 9/1983 | Bir | |
| 4,448,058 A | 5/1984 | Jaffe et al. | |
| 4,449,525 A | 5/1984 | White et al. | |
| 4,481,944 A | 11/1984 | Bunnell | |
| 4,499,914 A | 2/1985 | Schebler | |
| 4,502,481 A * | 3/1985 | Christian | 128/205.24 |
| 4,519,399 A | 5/1985 | Hori | |
| 4,530,334 A | 7/1985 | Pagdin | |
| 4,558,710 A | 12/1985 | Eichler | |
| 4,579,114 A | 4/1986 | Gray et al. | |
| 4,592,880 A | 6/1986 | Murakami | |
| 4,602,644 A * | 7/1986 | DiBenedetto et al. | 600/538 |
| 4,641,647 A | 2/1987 | Behan | |
| 4,644,947 A | 2/1987 | Whitwam et al. | |
| 4,648,398 A | 3/1987 | Agdanowski et al. | |
| 4,655,213 A * | 4/1987 | Rapoport et al. | 128/205.25 |
| 4,676,241 A * | 6/1987 | Webb et al. | 128/207.14 |
| 4,677,975 A | 7/1987 | Edgar et al. | |
| 4,686,974 A | 8/1987 | Sato et al. | |
| 4,747,403 A | 5/1988 | Gluck et al. | |
| 4,753,233 A * | 6/1988 | Grimes | 128/207.18 |
| 4,773,411 A | 9/1988 | Downs | |
| 4,774,946 A | 10/1988 | Ackerman et al. | |
| 4,782,832 A * | 11/1988 | Trimble et al. | 128/207.18 |
| 4,795,314 A | 1/1989 | Prybella et al. | |
| 4,802,485 A | 2/1989 | Bowers et al. | |
| 4,819,629 A | 4/1989 | Jonson | |
| 4,827,922 A | 5/1989 | Champain et al. | |
| 4,827,964 A | 5/1989 | Guido et al. | |
| 4,838,258 A | 6/1989 | Dryden et al. | |
| 4,856,506 A | 8/1989 | Jinotti | |
| 4,870,960 A | 10/1989 | Hradek | |
| 4,870,963 A | 10/1989 | Carter | |
| 4,875,718 A * | 10/1989 | Marken | 285/148.15 |
| 4,878,491 A | 11/1989 | McGilvray | |
| 4,913,401 A | 4/1990 | Handke | |
| 4,915,105 A | 4/1990 | Lee | |
| 4,919,128 A * | 4/1990 | Kopala et al. | 128/207.18 |
| 4,928,684 A | 5/1990 | Breitenfelder et al. | |
| 4,938,210 A | 7/1990 | Shene | |
| 4,938,212 A | 7/1990 | Snook et al. | |
| 4,944,310 A | 7/1990 | Sullivan | |
| 4,957,107 A | 9/1990 | Sipin | |
| 4,971,050 A | 11/1990 | Bartos | |
| 4,986,269 A | 1/1991 | Hakkinen | |
| 4,989,599 A | 2/1991 | Carter | |
| 5,005,571 A | 4/1991 | Dietz | |
| 5,009,635 A | 4/1991 | Scarberry | |
| 5,024,219 A | 6/1991 | Dietz | |
| 5,046,491 A | 9/1991 | Derrick | |
| 5,048,515 A | 9/1991 | Sanso | |
| 5,062,420 A * | 11/1991 | Levine | 128/204.18 |
| 5,063,922 A | 11/1991 | Hakkinen | |
| 5,063,938 A | 11/1991 | Beck et al. | |
| 5,065,756 A * | 11/1991 | Rapoport | 128/204.18 |
| 5,099,837 A | 3/1992 | Russel, Sr. et al. | |
| 5,105,354 A | 4/1992 | Nishimura | |
| 5,107,830 A | 4/1992 | Younes | |
| 5,107,831 A | 4/1992 | Halpern et al. | |
| 5,117,819 A * | 6/1992 | Servidio et al. | 128/204.18 |
| 5,129,390 A | 7/1992 | Chopin et al. | |
| 5,134,995 A * | 8/1992 | Gruenke et al. | 128/204.23 |
| 5,137,017 A | 8/1992 | Salter | |
| 5,148,802 A | 9/1992 | Sanders et al. | |
| 5,161,525 A | 11/1992 | Kimm et al. | |
| 5,165,398 A | 11/1992 | Bird | |
| 5,178,138 A | 1/1993 | Walstrom et al. | |
| 5,183,983 A | 2/1993 | Knop | |
| 5,195,528 A | 3/1993 | Hok | |
| 5,199,424 A | 4/1993 | Sullivan et al. | |
| 5,203,343 A | 4/1993 | Axe et al. | |
| 5,230,330 A | 7/1993 | Price | |
| 5,231,979 A | 8/1993 | Rose et al. | |
| 5,231,983 A | 8/1993 | Matson et al. | |
| 5,239,994 A | 8/1993 | Atkins | |
| 5,239,995 A | 8/1993 | Estes et al. | |
| 5,243,971 A * | 9/1993 | Sullivan et al. | 128/205.25 |
| 5,245,995 A | 9/1993 | Sullivan et al. | |
| 5,259,373 A | 11/1993 | Gruenke et al. | |
| 5,271,391 A | 12/1993 | Graves | |
| 5,280,784 A | 1/1994 | Kohler | |
| 5,293,864 A | 3/1994 | McFadden | |
| 5,303,698 A | 4/1994 | Tobia et al. | |
| 5,303,700 A | 4/1994 | Weismann et al. | |
| 5,305,787 A | 4/1994 | Thygesen | |
| 5,311,875 A | 5/1994 | Stasz | |
| 5,313,937 A | 5/1994 | Zdrojkowski | |
| 5,322,057 A | 6/1994 | Raabe et al. | |
| 5,335,654 A | 8/1994 | Rapoport | |
| 5,335,656 A | 8/1994 | Bowe et al. | |
| 5,343,878 A | 9/1994 | Scarberry et al. | |
| 5,353,788 A | 10/1994 | Miles | |
| 5,373,842 A | 12/1994 | Olsson et al. | |
| 5,388,571 A | 2/1995 | Roberts et al. | |
| 5,398,673 A | 3/1995 | Lambert | |
| 5,400,777 A | 3/1995 | Olsson et al. | |
| 5,404,871 A | 4/1995 | Goodman et al. | |
| 5,433,193 A | 7/1995 | Sanders et al. | |
| 5,443,061 A | 8/1995 | Champain et al. | |
| 5,458,137 A | 10/1995 | Axe et al. | |
| 5,479,920 A | 1/1996 | Piper et al. | |
| 5,490,502 A | 2/1996 | Rapoport et al. | |
| 5,492,113 A | 2/1996 | Estes et al. | |
| 5,503,146 A | 4/1996 | Froehlich et al. | |
| 5,507,535 A * | 4/1996 | McKamey et al. | 285/149.1 |
| 5,509,404 A | 4/1996 | Lloyd et al. | |
| 5,509,414 A | 4/1996 | Hok | |
| 5,517,983 A | 5/1996 | Deighan et al. | |
| 5,522,382 A | 6/1996 | Sullivan et al. | |
| 5,526,805 A | 6/1996 | Lutz et al. | |
| RE35,295 E | 7/1996 | Estes et al. | |
| 5,535,738 A | 7/1996 | Estes et al. | |
| 5,535,739 A | 7/1996 | Rapoport et al. | |
| 5,537,997 A | 7/1996 | Mechlenburg et al. | |
| 5,540,219 A | 7/1996 | Mechlenburg et al. | |
| 5,540,220 A | 7/1996 | Gropper | |
| 5,546,933 A | 8/1996 | Rapoport et al. | |
| 5,551,418 A | 9/1996 | Estes et al. | |
| 5,551,419 A | 9/1996 | Froehlich et al. | |
| RE35,339 E | 10/1996 | Rapoport | |
| 5,567,127 A | 10/1996 | Wentz | |
| 5,570,682 A | 11/1996 | Johnson | |
| 5,598,838 A | 2/1997 | Servidio et al. | |
| 5,608,647 A | 3/1997 | Rubsamen et al. | |
| 5,617,846 A | 4/1997 | Graetz et al. | |
| 5,632,269 A | 5/1997 | Zdrojkowski | |
| 5,633,552 A | 5/1997 | Lee et al. | |
| 5,642,730 A | 7/1997 | Baran | |

| | | | |
|---|---|---|---|
| 5,645,053 A | 7/1997 | Remmers et al. | |
| 5,645,054 A | 7/1997 | Cotner et al. | |
| 5,655,520 A | 8/1997 | Howe et al. | |
| 5,655,522 A | 8/1997 | Mechlenburg et al. | |
| 5,666,946 A | 9/1997 | Langenback | |
| 5,682,878 A | 11/1997 | Ogden | |
| 5,685,296 A | 11/1997 | Zdrojkowski et al. | |
| 5,701,883 A | 12/1997 | Hete et al. | |
| 5,704,345 A | 1/1998 | Berthon-Jones | |
| 5,715,812 A | 2/1998 | Deighan et al. | |
| 5,730,121 A | 3/1998 | Hawkins et al. | |
| 5,740,795 A | 4/1998 | Brydon | |
| 5,794,615 A | 8/1998 | Estes | |
| 5,823,187 A | 10/1998 | Estes et al. | |
| 6,044,844 A | 4/2000 | Kwok et al. | |
| 7,147,252 B2 * | 12/2006 | Teuscher et al. | 285/280 |
| 7,210,481 B1 * | 5/2007 | Lovell et al. | 128/205.25 |
| 2002/0096173 A1 | 7/2002 | Berthon-Jones et al. | |
| 2003/0154980 A1 | 8/2003 | Berthon-Jones et al. | |
| 2003/0217746 A1 * | 11/2003 | Gradon et al. | 128/201.26 |

FOREIGN PATENT DOCUMENTS

| | | |
|---|---|---|
| AU | A-33877/93 | 4/1993 |
| AU | B-59270/90 | 5/1993 |
| AU | A-38508/93 | 7/1993 |
| AU | A-48748/93 | 9/1993 |
| AU | A-52628/93 | 7/1994 |
| AU | B 79174/94 | 6/1995 |
| AU | A-34471/95 | 2/1996 |
| AU | A-40711/95 | 4/1996 |
| AU | B 34354/95 | 5/1996 |
| AU | A 39130/95 | 6/1996 |
| DE | 459104 | 4/1928 |
| DE | 701 690 | 1/1941 |
| DE | 3015279 A1 | 10/1981 |
| DE | 34 02 603 A1 | 8/1985 |
| DE | 3537507 A1 | 4/1987 |
| DE | 3539073 A1 | 5/1987 |
| DE | 4432219 C1 | 4/1996 |
| EP | 0 062 166 A2 | 10/1982 |
| EP | 0 066 451 A1 | 12/1982 |
| EP | B1 0 088 761 | 9/1983 |
| EP | 0 164 500 A2 | 3/1985 |
| EP | 0 171 321 A1 | 2/1986 |
| EP | 0 185 980 | 7/1986 |
| EP | 0 236 850 A2 | 9/1987 |
| EP | 0 872 643 A2 | 3/1988 |
| EP | 298 367 A2 | 1/1989 |
| EP | 0363530 A1 * | 4/1990 |
| EP | 0 388 525 A1 | 9/1990 |
| EP | 0 425 092 A1 | 5/1991 |
| EP | 0 481 459 A1 | 4/1992 |
| EP | 0549299 A2 | 6/1993 |
| EP | 606 687 A2 | 7/1994 |
| EP | 0705615 A1 | 9/1994 |
| EP | 0 714 670 A2 | 12/1994 |
| EP | 0 656 216 A2 | 6/1995 |
| EP | 0 661 071 A1 | 7/1995 |
| EP | 178 925 A2 | 4/1996 |
| EP | 0 709 107 A1 | 5/1996 |
| EP | 0 788 805 A2 | 8/1997 |
| EP | 0 839 545 A1 | 5/1998 |
| FR | 2 574 657 A1 | 6/1986 |
| FR | 2 672 221 | 8/1992 |
| FR | 2682042 A1 | 4/1993 |
| GB | 1432572 | 4/1976 |
| GB | 1 444 053 | 7/1976 |
| GB | 2 077 444 A | 12/1981 |
| GB | 2147506 | 9/1984 |
| GB | 2 147 506 A | 5/1985 |
| GB | 2 164 569 A | 3/1986 |
| GB | 2 205 167 A | 11/1988 |
| GB | 2 254 700 A | 10/1992 |
| GB | 2 271 811 A | 4/1994 |
| GB | 2 294 400 A | 5/1996 |
| JP | 54-104369 | 8/1979 |
| JP | 60-212607 | 10/1985 |
| JP | 62-103297 | 4/1987 |
| JP | 63-275352 | 11/1988 |
| JP | 2-173397 | 12/1988 |
| JP | 4-70516 | 3/1992 |
| JP | 4-70516 A | 3/1992 |
| JP | 6-249742 A | 9/1994 |
| JP | 06249741 A | 9/1994 |
| JP | 07280609 A | 10/1995 |
| JP | 8019610 A | 1/1996 |
| SE | 467041 B | 5/1992 |
| SU | 1710064 A1 | 2/1992 |
| WO | WO 80/01044 | 5/1980 |
| WO | WO 82/03326 | 10/1982 |
| WO | WO 82/03548 | 10/1982 |
| WO | WO 86/05965 | 10/1986 |
| WO | WO 86/06969 | 12/1986 |
| WO | WO 88/10108 | 12/1988 |
| WO | WO 90/14121 | 11/1990 |
| WO | WO 92/11054 | 7/1992 |
| WO | WO 92/15353 | 9/1992 |
| WO | WO 92/22244 | 12/1992 |
| WO | WO 93/08857 | 5/1993 |
| WO | WO 93/09834 | 5/1993 |
| WO | WO 93/21982 | 11/1993 |
| WO | WO 93/24169 | 12/1993 |
| WO | WO 94/16759 | 8/1994 |
| WO | WO 94/20051 | 9/1994 |
| WO | WO 94/23780 | 10/1994 |
| WO | WO 95/32016 | 11/1995 |
| WO | WO 96/16688 | 6/1996 |
| WO | WO 96/40337 | 12/1996 |
| WO | WO 97/02064 | 1/1997 |
| WO | WO 97/10019 | 3/1997 |
| WO | WO 97/10868 | 3/1997 |
| WO | WO 97/15343 | 5/1997 |
| WO | WO 97/28838 | 8/1997 |
| WO | WO 97/41812 | 11/1997 |
| WO | WO 98/06449 | 2/1998 |
| WO | WO 98/25662 | 6/1998 |
| WO | WO 98/33433 | 8/1998 |
| WO | WO 98/35715 | 8/1998 |
| WO | WO 98/36245 | 8/1998 |
| WO | WO 98/36338 | 8/1998 |
| WO | WO 98/47554 | 10/1998 |
| WO | WO 98/57691 | 12/1998 |

OTHER PUBLICATIONS

Int'l. Appn. No. PCT/US79/01063 filed Nov. 27, 1979—WO 8001044, May 29, 1980.
Search Report for EP Application No. 92311645.3, filed Dec. 21, 1992.
Derwent: Flowmeter for fluids-has turbine transducer and volumetric sensor for simultaneous calibration.
Mark Kantrowitz, Erik Horskotte and Cliff Joslyn; "Answers to Frequently Asked Questions about Fuzzy Logic and Fuzzy Expert Systems" Version 1.24 last Modified Feb. 20, 1996.
New! Breas PV 100 CPAP First Class Quality and Function. At the right Price; Jul. 4, 1998, pp. 1-2.
PV 101 BI Level CPAP and PV 102 Bi-Level Time; pp. 1-3.
Prodigy Medical Supplies Co. Ltd.; CPAP.
Puritan Bennett; Companion 318 Nasal CPAP System; May 1993.
Nellcor Puritan Bennett; Announcing the Goodnight 314 and GoodKnight 318 Nasal CPAP Systems.
Puritan Bennett: Clean, Quiet, and Comfortable . . . The Companion's 515 Nasal CPAP System; Jun. 1988.
DeVilbiss Night Guard Nasal CPAP for the Treatment of Obstructive Sleep Apnea.
Sunrise; DeVilbiss Horizon LT 8001 Nasal CPAP Therapy Small in Size, big on features; Aug. 1997.
Devilbiss: Revitalizer Soft Start; The Facts Speak for Themselves, 1992.
Tranquility; Performance CPAP Advantage.
Healthdyne International; Tranquility Plus.
Respironics Inc.; Respironics' Solo CPAP System Provides Simplified OSA Therapy at an Outstanding value; Sep. 19, 1996.
Respironics Inc.; The First Family of OSA Therapy; 1991.
Fisher & Paykel Healthcare; HC200 Series Nasal CPAP Blower & Heated Humidifier.

Pierre Medical; Morphee Plus appareil de traitement des apnees du sommeil manuel d'utilisation.

Weinmann:Hamburg; Somnotron nCPAP-Great WM 2300, Nov. 1991.

Puritan Bennett; 515a Part of Our Blueprint for the Future; Mar. 1990.

Puritan Bennett; Companion 320 I/E Bi-Level Respiratory System: Apr. 1993.

ResMed; Sullivan VPAP II & II ST.

ResMed; The Sullivan V Family of CPAP Systems; 1996.

ResMed; The AutoSet Portable II; 1997.

ResMed: Sullivan Nasal CPAP System.

ResMed; The Sullivan IIID; 1995.

ResMed; The Sullivan Comfort; 1996.

DeVilbiss a Division of Sunrise Medical; Expand your Horizons With the Horizons; 1995.

Healthdyne Technologies; Home Health Care Dealer; The Journal of Home Medical Equipment and Serives/Supplier; Nov. and Dec. 1997.

Healthdyne International; Tranquility Quest, The Compact CPAP for Greater patient comfort.

AirStep; Medical Products . . . Stand the Test of Time.

MAP Medical Progress for Physician und Patient; The Gentle Therapy for Sleep-Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnea Therapy with Somnotron 3 and Somno-Mask System.

Respironics Inc.; Aria CPAP System; 1993.

Respironics Inc.; SleepEasy III A New Dawn in Patient Compliance.

Respironics Inc.; Muliple Choice REMstar Choice Nasal CPAP System.

MaxII nCPAP and Moritz II Bi-Level Brochure.

* cited by examiner

PATIENT INTERFACE ASSEMBLY FOR CPAP RESPIRATORY APPARATUS

CROSS REFERENCE TO RELATED APPLICATIONS

This application is a continuation of U.S. application Ser. No. 10/385,701, filed Mar. 12, 2003, allowed, which is a divisional of U.S. application Ser. No. 08/524,148, filed Sep. 6, 1995, now abandoned, which is a continuation of U.S. application Ser. No. 07/994,153, filed Dec. 21, 1992, now abandoned, which claims priority to Australian Application No. PL 0148, filed Dec. 20, 1991, each of which is incorporated herein by reference in its entirety.

The present invention relates to an improved CPAP respiratory apparatus which will increase patient comfort and therefore compliance.

The fundamental disclosure of CPAP is made in the specification of PCT/AU82/00063 published under WO 82/03548 which discloses the supply of air to the nose of the patient at an elevated pressure, the air being supplied through a large bore inlet tube. The elevated pressure at which the air is supplied is approximately 10 cm water gauge although pressures in the range of approximately 5-20 cm water gauge are encountered. However, this pressure is measured while the patient is not breathing and as the patient inspires and expires the pressure in the patient's mask rises and falls typically by approximately 1-2 cm above and below the steady state level. The large bore inlet tube has an unrestricted internal diameter of approximately 20 mm and thus does not introduce unacceptably high pressure drops and swings in the gas delivery system during breathing. All commercially available devices have standardised to this size and arrangement.

For the patient, the work of breathing increases in proportion to the size of the pressure swing during the respiration cycle. In particular, the discomfort experienced by the patient also increases in proportion to the increase in mask pressure during breathing out. In order to deliver the patient's breathing air requirements without significant pressure loss in the supply tube, which would create a relatively large pressure swing during the breathing cycle, the delivery tube and inlet to the nose mask were selected to be substantially unrestricted and to have the large bore of approximately 20 mm.

However, this arrangement and tubing size are not particularly convenient as far as the comfort of the patient and control of the treatment are concerned. In practice, patients wearing nose masks or equivalent devices including such tubing can turn only from side to side and the freedom of movement of the patient is impaired by the tubing. If the tubing and nose mask could be made smaller, and more acute changes in the direction of air flow tolerated, a much more comfortable and acceptable air delivery system would result. Also if a humidifier and/or a filter could be placed between the pump and the mask, then patient comfort could be increased. Similarly, if a flow measuring device could be so located, control of treatment could be enhanced.

It is the object of the present invention to substantially overcome or ameliorate the above mentioned difficulties by the provision of a CPAP respiratory apparatus which maintains the pressure of air or other breathable gas at the point of immediate access to the patient's respiratory system substantially constant notwithstanding in-line components which introduce appreciable pressure drops.

It is appreciated that increasing the resistance to flow in the supply tube results in an increased pressure drop between the "pump end" and "patient end" of the delivery tube. In order to compensate for this pressure drop between the ends of the delivery tube whilst maintaining flow, the present invention seeks to maintain the air pressure at the "patient end" substantially constant. This is done by sensing the pressure within the nose mask, or equivalent device, itself.

Two known commercially available CPAP respiratory devices involve some pressure or air flow control. One of these is the device sold by RESPIRONICS of the USA under the trade name BIPAP in which the supply pressure can be switched between a lower pressure and a higher pressure in accordance with the patient's respiratory cycle in order to assist the patient's breathing effort. This switching is achieved by sensing air flow through a sensor in the pump of the air supply system. Another commercially available device sold by HEALTHDYNE also of the USA has a control mechanism which controls the pressure at the outlet of the air pump.

Both of these commercially available devices use the standard large bore 20 mm inlet tubing which is substantially unrestricted downstream of the pump outlet and will not operate satisfactorily with pressure drop inducing components such as small bore tubing. This is thought (as will be apparent from the experimental data given hereafter) to be due to the large pressure drop which causes large pressure swings in the nose mask as the patient inspires and expires. In particular, because these prior art devices do not attempt to derive the signal to control the operation at the air pump as near to the patient's respiratory system as possible, and downstream or all pressure drop inducing components, there is a problem of time lags and phase shifts as regards the supply of air to and from the patient. It has been experimentally determined by the applicant that by sensing the pressure at the patient's mask and servo-controlling same to be substantially constant, the problems introduced by the pressure drop created in the supply tubing, can be substantially overcome.

In accordance with the first aspect of the present invention there is disclosed a CPAP respiratory apparatus comprising a breathable gas delivery device adapted to deliver breathable gas to the inlet of a patient's respiratory system, a breathable gas supply means having an outlet and arranged to supply breathable gas to said outlet at a pressure above atmospheric pressure, and a flexible conduit having an internal bore and being connected between said outlet and said gas delivery device wherein a pressure transducer is connected to said device to sense the pressure at said respiratory system inlet, and a servo-controller is connected to both said gas supply means and said pressure transducer to adjust the operation of said gas supply means to maintain the pressure at said respiratory system inlet substantially constant.

Preferably, at least that portion of said conduit closest to said nose mask has an internal bore which is relatively small compared with the remainder of the conduit.

In accordance with a second aspect of the present invention there is disclosed a method of operating a breathable gas supply means of a CPAP respiratory apparatus comprising a breathable gas delivery device adapted to deliver breathable gas to the inlet of a patient's respiratory system and connected by a flexible conduit to an outlet of said gas supply means to receive breathable gas therefrom at a pressure above atmospheric pressure, said method comprising the steps of sensing the pressure supplied to said respiratory system inlet by said gas delivery device, and using the sensed pressure to servo-control said gas supply means to maintain the pressure at said respiratory system inlet substantially constant.

Preferably, at least one pressure drop inducing device is located in the gas supply line between the pump and patient.

Some embodiments of the present invention will now be described with reference to the drawings in which.

Figure 1:
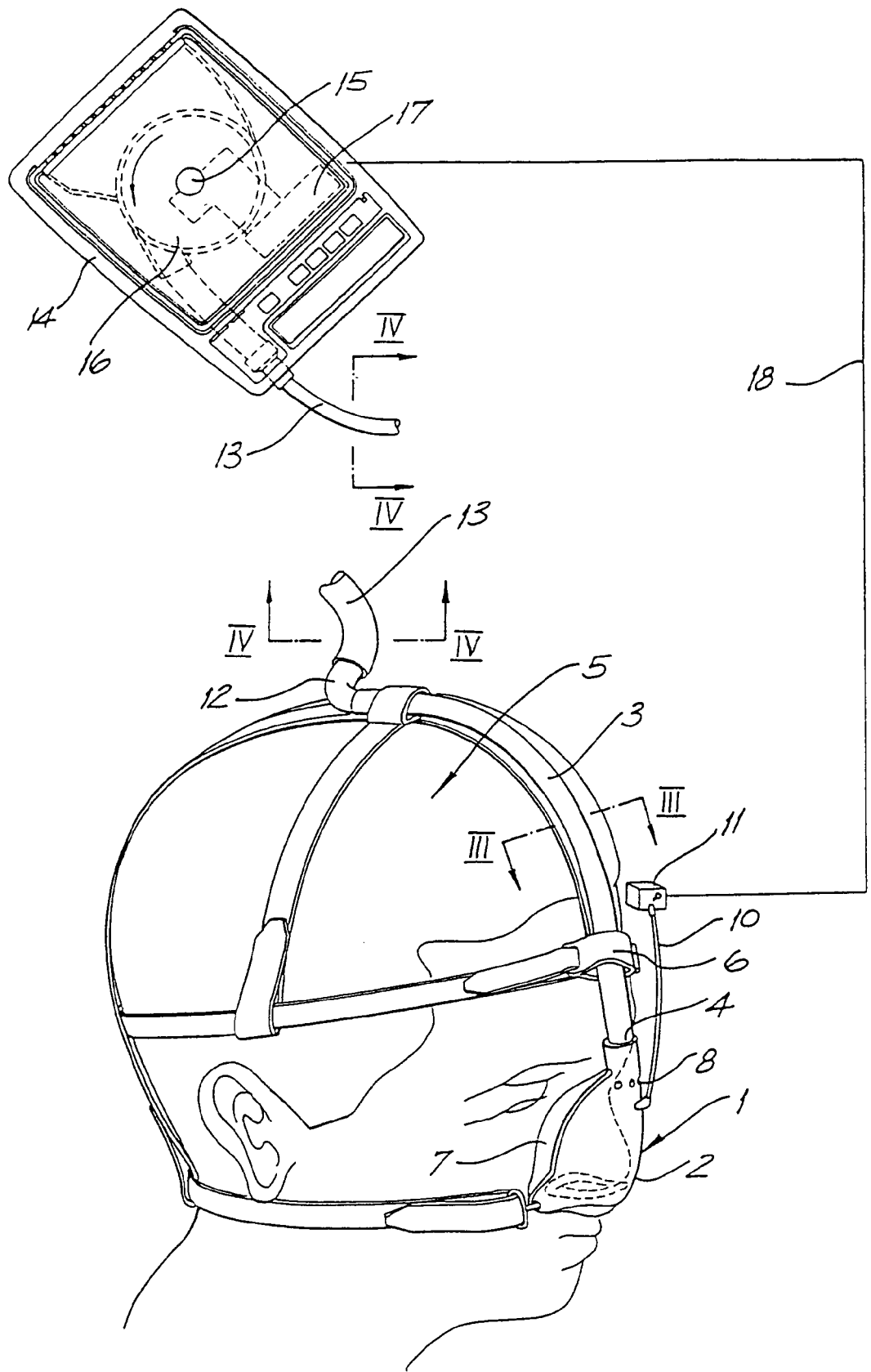
FIG. 1 is a schematic perspective view of the nose mask and air supply tube of the CPAP respiratory apparatus of a first embodiment.
Figure 2:
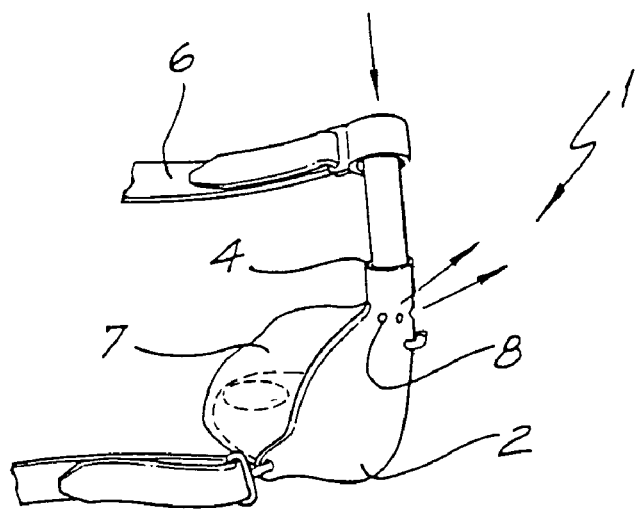
FIG. 2 is a partial perspective view of the mask only with its membrane distended.

As seen in FIG. 1 a nose mask 1 is of generally known configuration and is substantially as disclosed in Australian Patent Application No. 77110/91. The mask 1 takes the form of a shell 2 of firm plastics which is shaped to fit over at least the nose region of the patient. A distendable membrane 7 is mounted on the shell 2 and forms a face contacting portion for the mask 1. The shell 2 and membrane 7 together define a chamber which receives the patient's nose. The chamber communicates with an air or other breathable gas supply aperture to which a short length of supply tube 3 is connected. The aperture is preferably provided with a swivel joint 4 so that the supply tube 3 can rotate relative to the remainder of the face mask 1. This prevents the supply tube 3 from becoming inadvertently twisted. The nose mask 1 is retained on the patient 5 by means of conventional straps 6.

In the vicinity of the swivel joint 4 are located a series of apertures 8 through which air or other breathable gas exits to atmosphere as indicated by the arrows in the drawing. Pressure is sensed in the interior chamber of mask 1 by a thin flexible pipe 10 which is connected a pressure transducer 11 which provides an electrical output signal carried on cable 18 to a servo-controller 17 for the pump 14.

Figure 3:
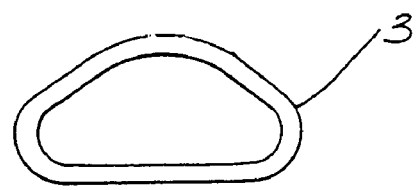
FIGS. 3 and 4 are cross-sectional views along the lines III-III and IV-IV of FIG. 1 respectively.
Figure 4:
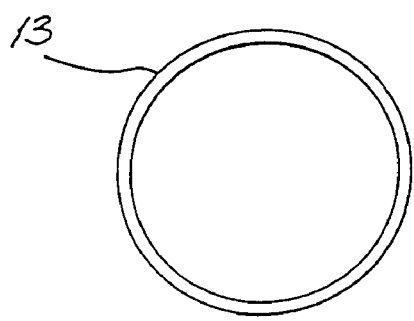

The supply tube 3 is of a small bore (typically having an effective internal diameter of 9-15 mm) and thus the patient whilst sleeping cannot roll onto an uncomfortable large bore tube. As indicated in FIG. 3 the small bore supply tube 3 in this embodiment has a substantially triangular cross-sectional shape and is flexible. The term "effective internal diameter" means the diameter of a tube of circular internal cross-sectional shape which has the same internal cross-sectional area.

Preferably a swivel joint 12 connects the small bore supply tube 3 to a substantially conventional large bore supply tube 13. The pipe 10 which typically has a very small bore or the cable 18 can conveniently be connected alongside the supply tubes 3, 13. This supports the pipe 10 yet enables the pressure transducer 11 to be located either at, or remote from, the nose mask 1. If desired, the pipe 10 and tube 3 can be combined in a single moulding as indicated by broken lines on FIG. 3.

Alternatively, if the pressure transducer 11 is located within, or adjacent to, the mask the electrical outputs signal cable 18 of the transducer can be conveyed to the servo-controller 17 via small pipe 10.

The large bore supply tube 13 is connected to a pump 14 which consists essentially of an electric motor 15 and fan 16. The pump 14 preferably supplies air, however, other breathable gases such as mixtures of air and oxygen can be supplied in known fashion. The term "air" shall be used hereafter for such gases. The electric motor 15 is controlled by a substantially conventional servo-controller 17 which receives as an input, the output from the pressure transducer 11. If desired, the pipe can be sufficiently long to locate the transducer 11 at the pump 14.

It will be apparent to those skilled in the art that the pressure transducer 11 and servo controller 17 enable the operation of the electric motor 15 to be controlled so as to maintain the air pressure within the nose mask 1 substantially constant. As a result, the electric motor 15 accommodates in its operation the fluctuating internal pressure drop created by both the patient's breathing and the small bore of the supply tube 3. In particular, the supply conduit interconnecting the mask 1 and air pump 14 can now have a small bore (in the range of from 9 to 15 mm in internal diameter) over at least part of its length, particularly over that section in the region of the patient's face and head. This represents a decrease in available cross-sectional area of the supply tube 3 from 43.75% to 79.75% respectively.

Because the supply tube 3 has such a reduced bore, the tube is much more flexible and comfortable for the user and can conveniently be fixed to the straps 6 used for holding the nose mask on the patient's face. In particular, it is not generally possible to lie upon the 20 mm large bore tubing without feeling discomfort, however, with the relatively small bore supply tube 3 this is possible. As a consequence the patient's comfort is substantially increased. This increases the patient's compliance, especially after the more pronounced symptoms of sleep apnea have been initially ameliorated. The increased compliance is of particular importance in the long term treatment of the patient.

Comparative Tests

The above described apparatus was tested alongside the above. mentioned commercially available BIPAP (Respironics) device and TRANQUILITY PLUS device (the trade name of the Healthdyne product).

For the experiment, the large bore supply tube 13 took the form of standard 20 mm bore tubing. The length of the small bore supply tube 3 was 17 cm. All three units were tested with the same breathing simulator which delivered a substantially sinusoidal air flow having a 500 ml tidal volume at 12 cycles/minute. The peak flow during both inspiration and expiration was 50-60 litres per minute.

For each air pump arrangement (BIPAP, TRANQUILITY PLWS and air pump 14) three types of masks were used. The first was a conventional mask with a 20 mm constant diameter supply tube (in the case of BIPAP and TRANQUILITY PLUS the mask and tube were as supplied with the equipment). The second mask was the mask 1 with the supply tube 3 being of circular cross-section and of 15 mm internal diameter. The third mask was the mask 1 but with 9 mm internal diameter or the supply tube 3.

The results for 5 different levels of CPAP pressure (0, 5, 10, 15 and either 17 or 20 cm water gauge) are set out in Table 1, the figures given are air pressures in cm of water gauge with $P_{stat}$ being the average or static pressure within the mask whilst $\Delta P_{tot}$ is the combined pressure swing during the inspiration/expiration cycle of the breathing simulator.

It can be seen that the combined pressure swing $\Delta P_{tot}$ increases significantly with decreasing tubing diameter with the HEALTHDYNE and BIPAP units, while the servo-controlled unit 14 maintains pressure in the mask 1 generally to better than 1 cm total swing for all sizes of tubing. It follows therefore that an improved result allowing the use of the more comfortable small bore tubing, has been achieved.

Figure 5:
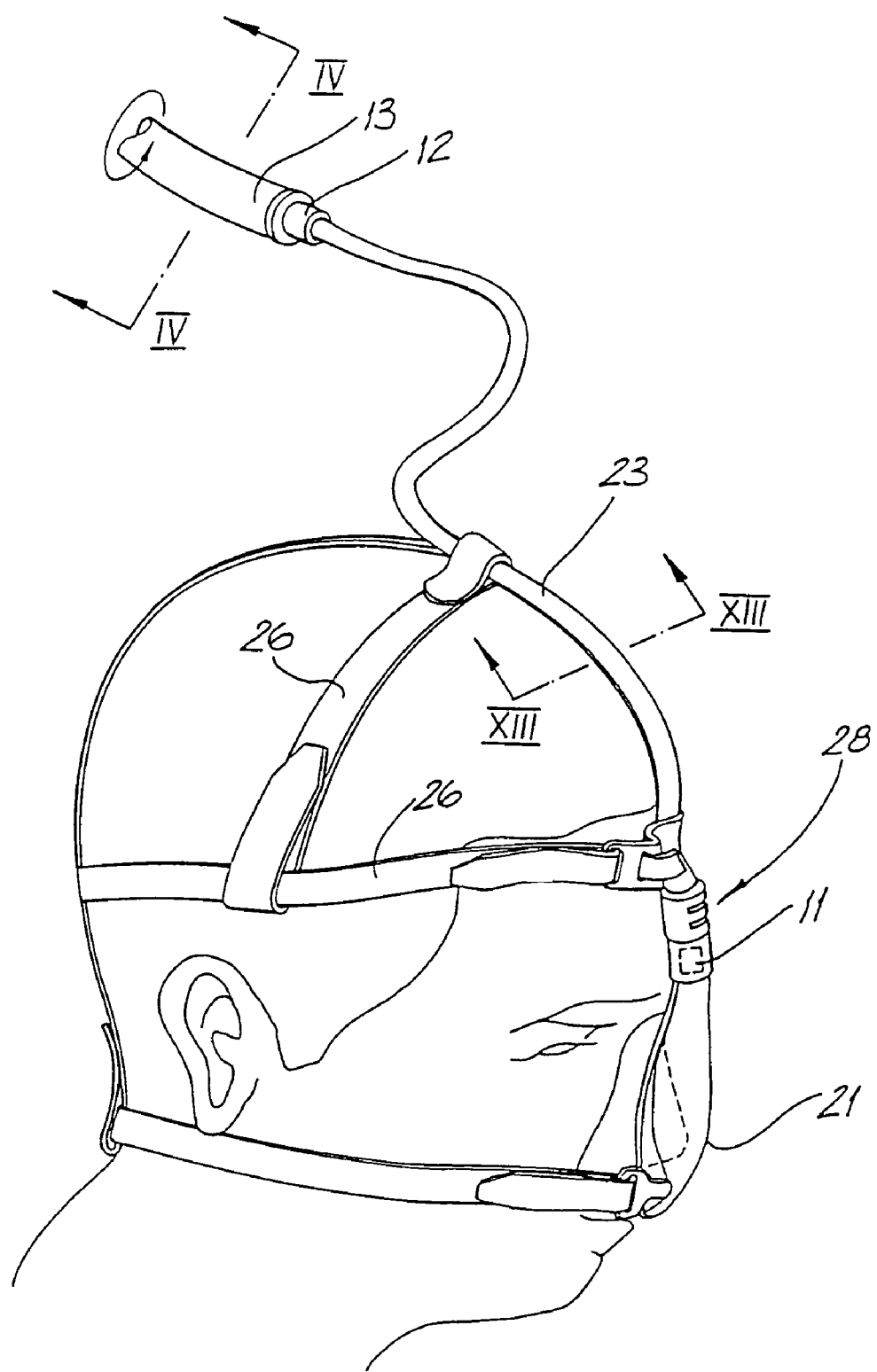
FIG. 5 is a perspective view of the nose mask, harness and supply conduit of a second embodiment.
Figure 13:
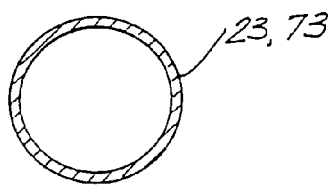
FIG. 13 is a cross-sectional view taken along the line XIII-XIII of FIGS. 5, 6 and 11.

A second embodiment is illustrated in FIG. 5 where like parts are indicated by a designator increased in magnitude by 20. Thus, the mask 21 of the second embodiment is a face mask and includes a pressure transducer 11 located within the mask 21 as indicated by broken lines in FIG. 5. The transducer 11 is located within the mask 21 and between the patient's nose and the apertures 8. A substantially similar arrangement of straps 26 retains the nose mask 21 in position. As indicated in FIG. 13, the cross-sectional shape of the small bore inlet tube 23 is circular. Again, the small bore inlet tube 23 is connected to the conventional large bore inlet tube 13 by means of a substantially conventional swivel joint 12.

Figure 6:
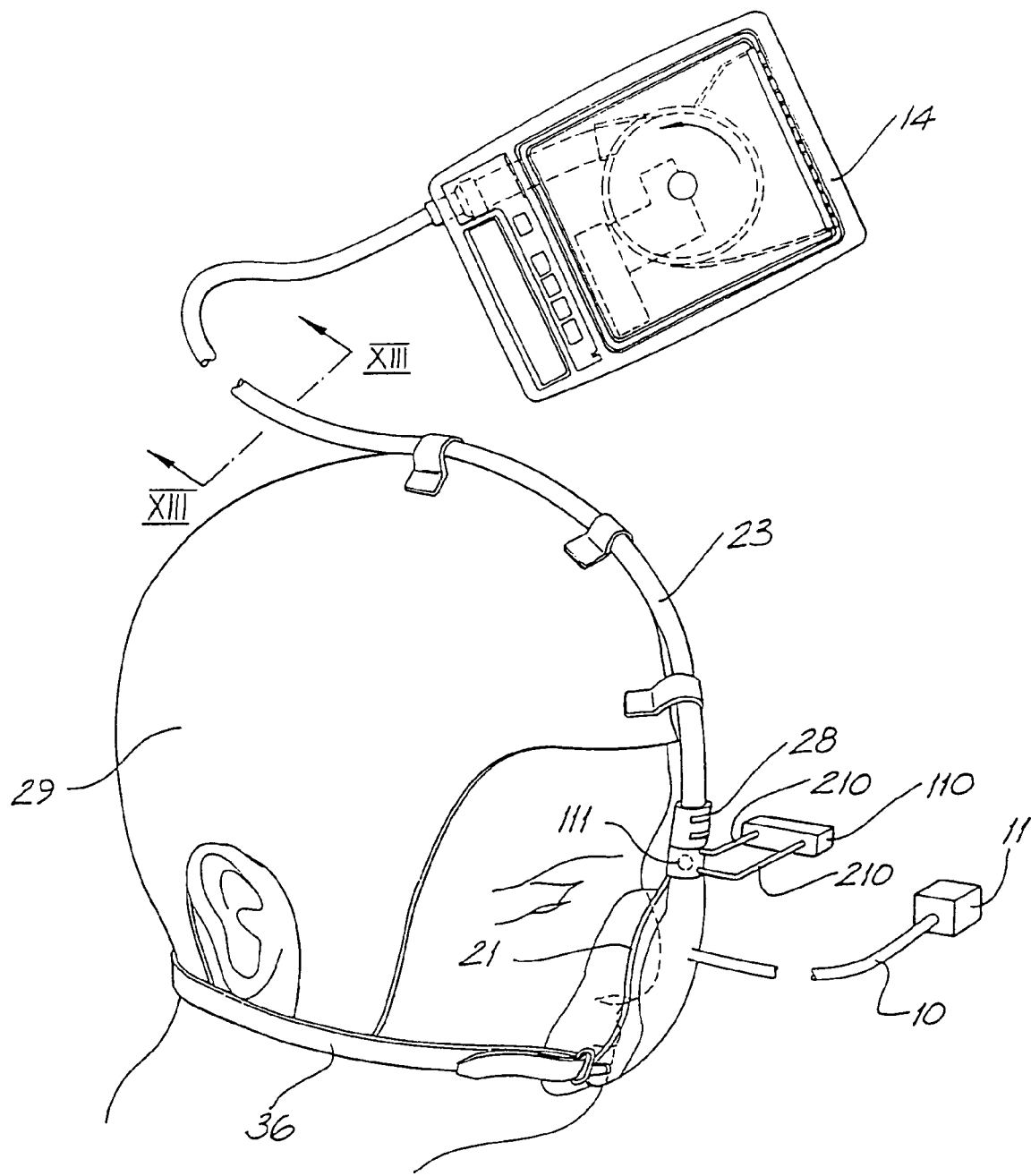
FIG. 6 is a view similar to FIG. 5, but of a third embodiment.

A third embodiment is illustrated in FIG. 6 in which the nose mask 21 and small bore inlet tube 23 are substantially as in FIG. 5. However, a flow orifice 111 (preferably of the type disclosed in U.S. Pat. No. 4,006,635 [Billette]) only is located in the mask 21 and is connected by two small tubes 210 to a flow transducer 110. The tubes 210 are located one upstream and one downstream of the flow orifice 111. As before, the pressure transducer 11 is connected to the mask 21 via the tube 10. In addition, a cap 29 with straps 36 is provided for the patient in order to secure the small bore inlet tube 23.

Figure 7:
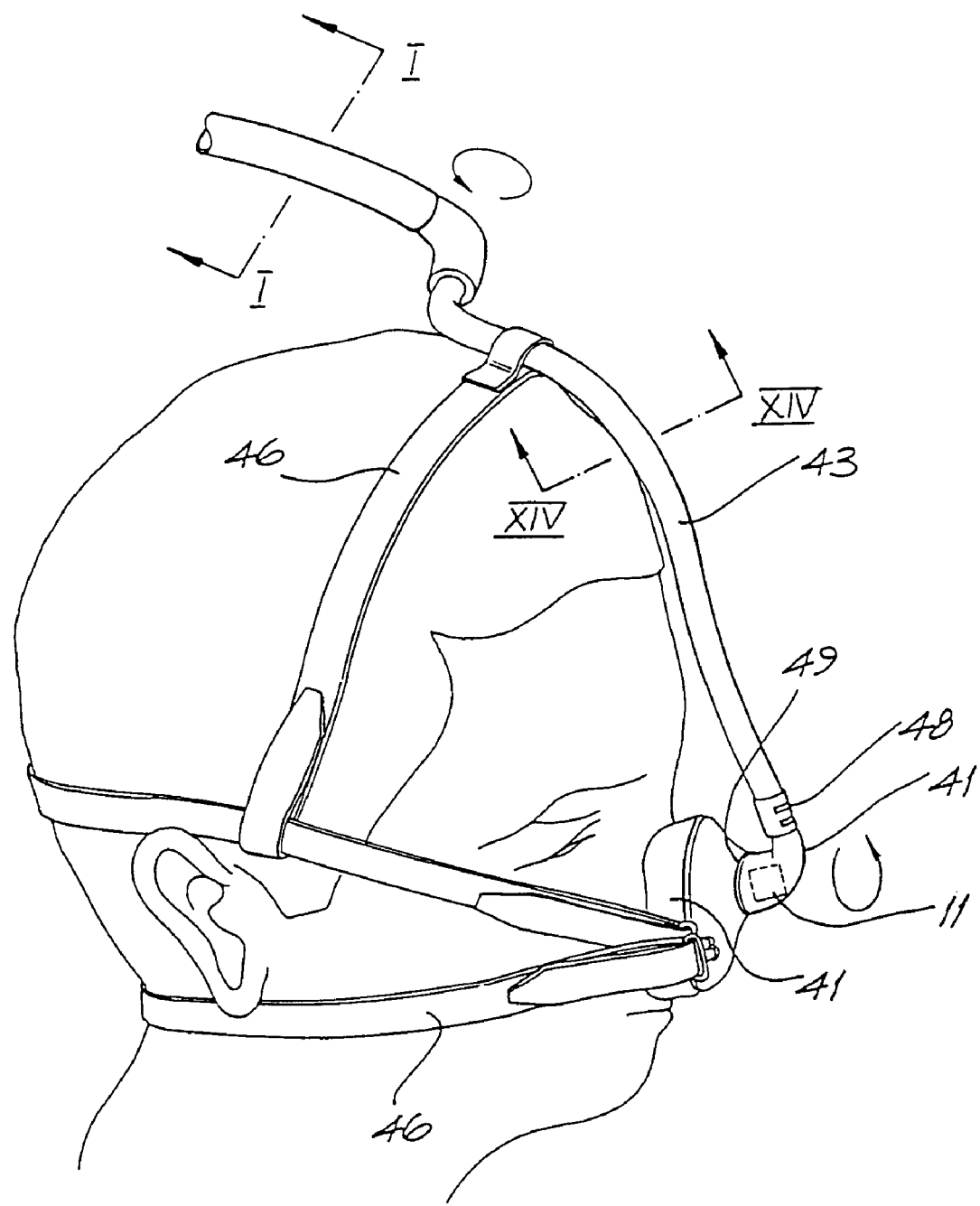
FIG. 7 is a view similar to FIG. 5, but of a fourth embodiment.

A fourth embodiment is illustrated in FIG. 7 in which like parts have their designator increased in magnitude by 40 relevant to the embodiment of FIG. 1. It will be seen that the configuration of the nose mask 41 is changed so as to provide a swivel joint 49 which is sufficiently large to accommodate the pressure transducer 11 which is again located downstream of the apertures 48. The configuration of the straps 46 is also different and provides an alternative securing arrangement.

Figure 8:
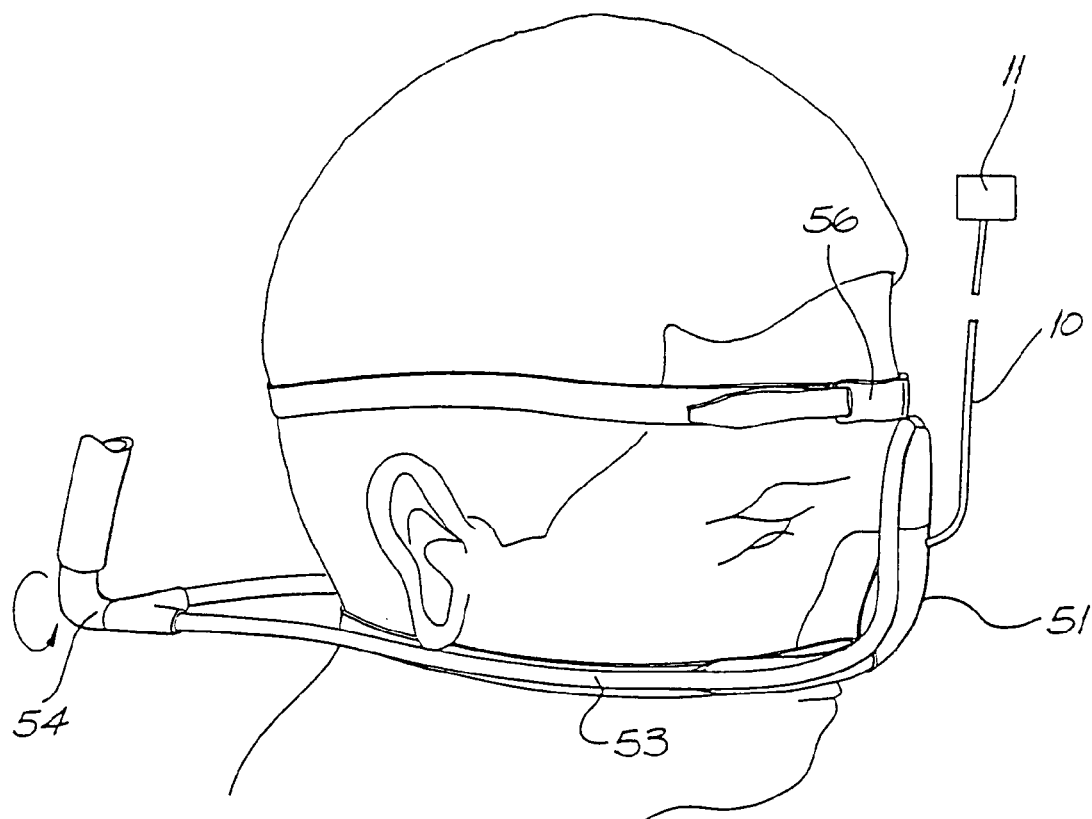
FIG. 8 is a view similar to FIG. 5, but of a fifth embodiment.
Figure 9:
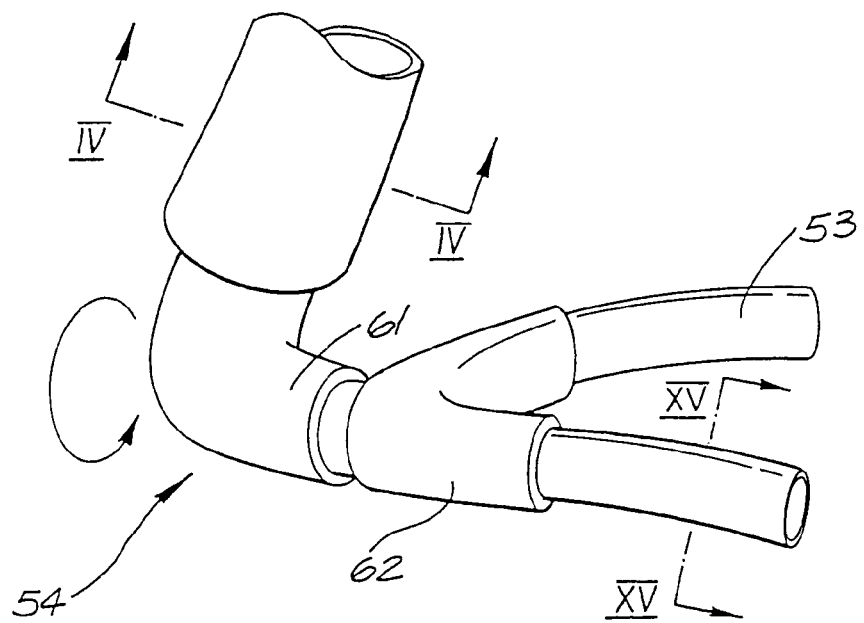
FIG. 9 is an enlarged view of the branched connector of FIG. 8.
Figure 10:
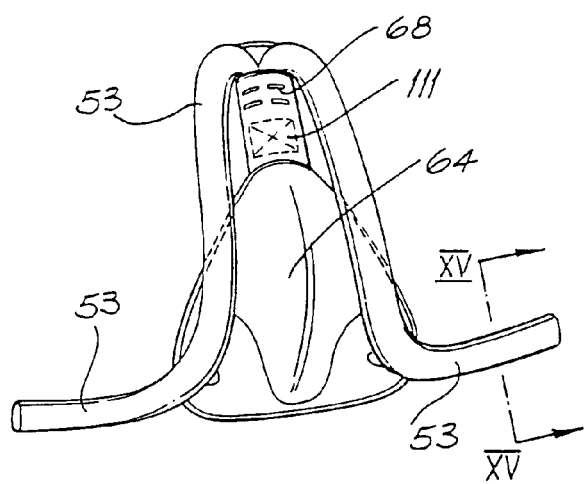
FIG. 10 is a front view of the nose mask of FIG. 8.

FIGS. 8-10 illustrate a fifth embodiment in which a nose mask 51 is supplied by means of a split or dual inlet tubes 53 each of which is supplied from a branch swivel connector 54 illustrated in more detail in FIG. 9. The connector 54 is located to the rear of the patient's head and the nose mask 51 is secured in position by means of a forehead strap 56.

As seen in FIG. 9, the branch connector 54 includes an elbow 61 which swivels as indicated by the arrow in FIG. 9, relative to a Y-piece 62. The inlet tubes 53 are sealed directly to the Y-piece 62.

Figure 15:
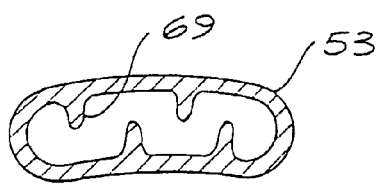
FIG. 15 is a cross-sectional view taken along the line XV-XV of FIGS. 9 and 10.

FIG. 10 illustrates further detail of the nose mask 51 and, in particular, illustrates the cavity 64 which receives the patient's nose, The flow orifice 111 is located within the inlet to the cavity 64 as are the exit apertures 68. It will be seen that the inlet tubes 53 extend across each cheek of the patient and alongside the nose mask 51. As seen in FIG. 15, the inlet tubes 53 preferably have a flat configuration and are provided with a plurality of internal ribs 69 which prevent the inlet tube 53 being crushed between the pillow and the patient's head.

Figure 11:
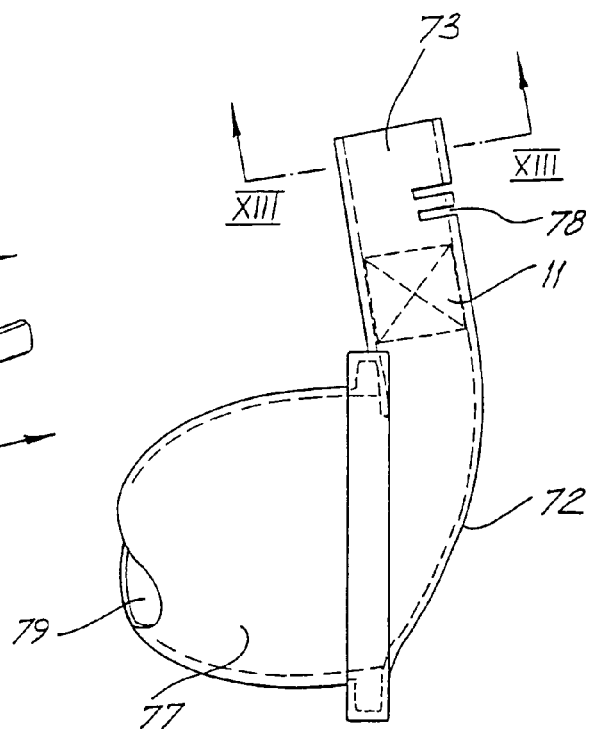
FIG. 11 is a side elevation of an alternative nose mask.
Figure 12:
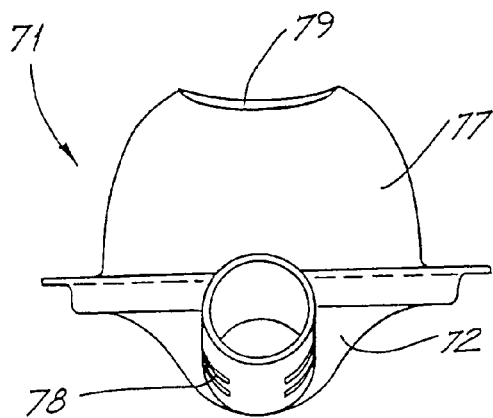
FIG. 12 is a plan view of the nose mask of FIG. 11.

Turning now to FIGS. 11 and 12, a still further embodiment of the nose mask 71 is illustrated. The nose mask 71 has a substantially rigid outer shell 72 which has an inlet 73 of substantially circular cross-section which includes exit apertures 78 and is sufficiently large to accommodate the pressure transducer 11 as illustrated (or the flow transducer 110—not illustrated). Sealingly connected to the outer shell 72 is a soft membrane 77 which is shown in FIGS. 11 and 12 in its distended position and has a nose receiving aperture 79. Once the nose of the patient is inserted into the aperture 79, the membrane 77 then conforms itself to the surface of the patient's skin thereby providing an effective seal.

Figure 14:
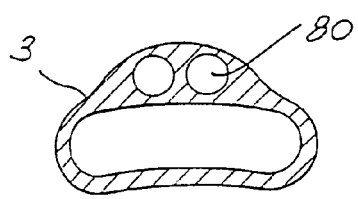
FIG. 14 is a cross-sectional view taken along the line XIV-XIV of FIG. 7.

As indicated in FIG. 14, if desired the inlet tube 3 and equivalents, can be provided with two internal passageways 80 which can be used either to transmit pressure from the region adjacent the patient's nose or to locate the electric cable(s) from transducer(s).

With the above described distendable mask, the deformable membrane has hitherto stretched and compressed with changes in the mask pressure. This oscillation is somewhat disturbing to the patient and is substantially eliminated in accordance with the above since the servo-controller 17 maintains the mask pressure substantially constant.

Furthermore, most of the noise escaping from a CPAP device comes either from the air inlet or air outlet. This can be reduced by placing baffles in the air inlet and/or the air outlet, but with the prior art devices this is at the expense of increasing the pressure drop and pressure swings in the mask during inspiration and expiration.

In accordance with the above described arrangements, this additional baffling can be added and the pressure swings that would otherwise result can be compensated for by servo-controlling the pressure in the mask. Since mask comfort and noise level are the two most important determinants of patient comfort and compliance, this represents a substantial advantage.

Figure 16:
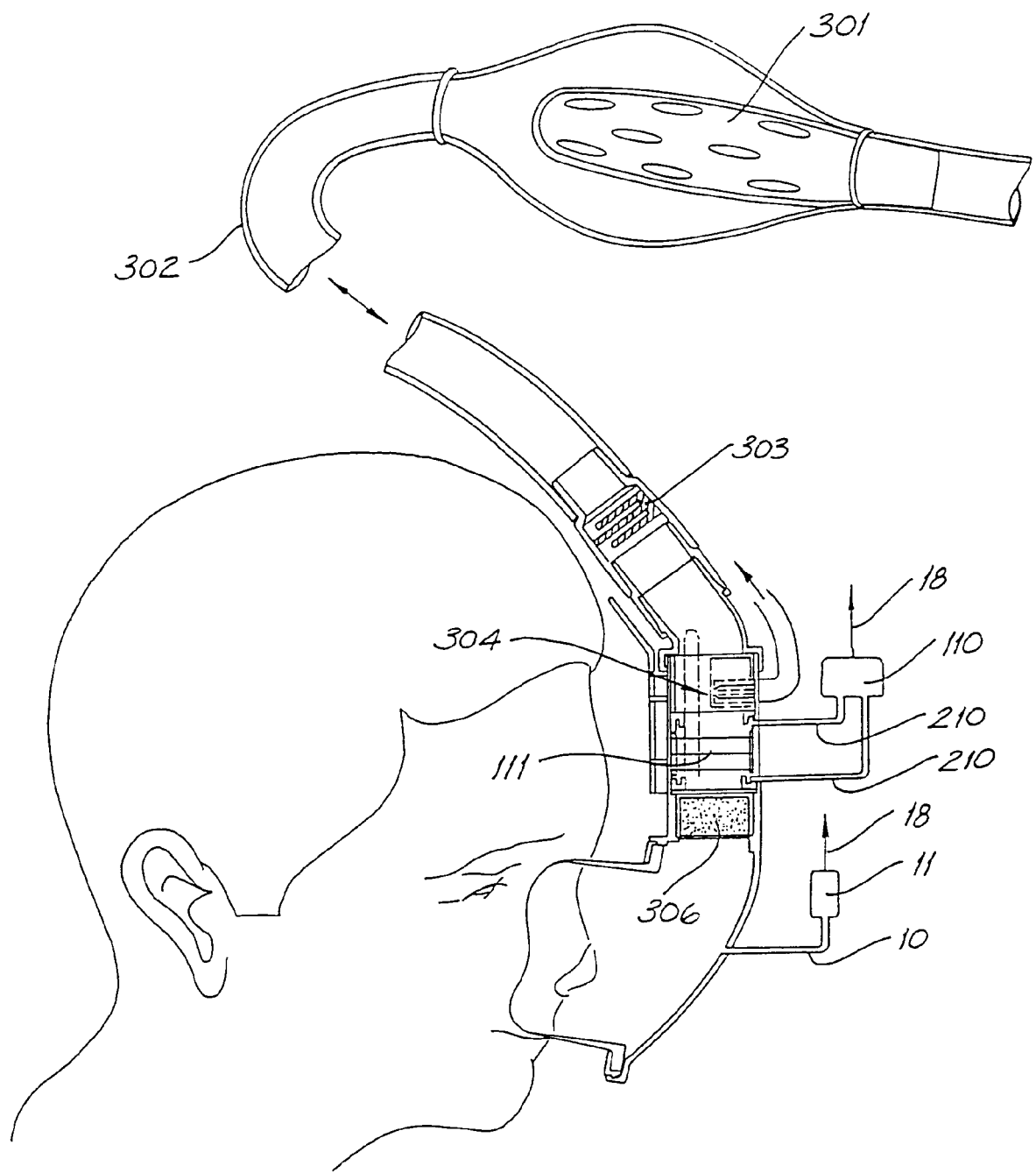
FIG. 16 is a view similar to FIG. 1 but illustrating a further embodiment having various different types of pressure drop inducing components.

Like the small bore tube 3,23 and the connector 54, such baffles represent pressure drop inducing components. As indicated in FIG. 16, such components can take the form of baffles 301, sharp bend: 302, a filter 303, a high pressure drop air outlet diffuser 304 having a diverting tube to direct flow away from a sleeping partner, a flow orifice 111 and a humidifier 306 such as a hydroscopic condensing humidifier made by ICOR AB of Sweden. The pressure drop introduced by any or all of these "accessories" can be accommodated so as to maintain the pressure at the patient's nose substantially constant.

If desired, the transducers 11,110 can be located at or near the mask as illustrated and connected by cables 18 to the control apparatus 17. Alternatively, the tubes 10,210 can be sufficiently long to enable the transducers 11,110 to be located adjacent the pump 14. This arrangement has the advantage that no electric cables are located near the patient.

In addition, if the positions of the flow orifice 111 and humidifier 306 shown in FIG. 16 are reversed, then a combined sensing arrangement is possible. In this arrangement the flow orifice 111 is connected to the flow transducer 110 as before via two tubes 210. The downstream one of the tubes 210 is branched to provide the tube 10 for the pressure transducer 11.

The foregoing describes only some embodiments of the present invention and modifications, obvious to those skilled in the art can be made thereto without departing from the scope of the present invention.

For example, although a nose mask is described and illustrated in detail, a full face mask or nasal prongs can also be used.

TABLE I

| | Pstat | ΔPtot | Pstat | ΔPtot | Pstat | ΔPtot | Pstat | ΔPtot | Pstat | ΔPtot |
|---|---|---|---|---|---|---|---|---|---|---|
| BIPAP UNIT | | | | | | | | | | |
| Conv. Mask | | | 5.0 | 1.00 | 10.0 | 1.20 | 15.0 | 1.40 | 20.00 | 2.40 |
| New Mask 15 | | | | 1.20 | | 1.30 | | 1.40 | | 2.00 |
| New Mask 9 | | | | 2.20 | | 2.70 | | 3.80 | | 5.40 |
| HEALTHDYNE TRANQUILITY PLUS | | | | | | | | | | |
| Conv. Mask | 0.0 | 0.70 | 5.0 | 0.85 | 10.0 | 1.10 | 15.0 | 1.35 | 17.00 | 1.40 |
| New Mask 15 | | 1.20 | | 1.40 | | 1.80 | | 2.10 | | 2.20 |
| New Mask 9 | | 2.20 | | 3.20 | | 4.20 | | 4.80 | | 5.10 |
| SERVO-CONTROLLED UNIT 14 | | | | | | | | | | |
| Conv. Mask | 0.0 | 0.40 | 5.0 | 0.35 | 10.0 | 0.45 | 15.0 | 0.60 | 20.00 | 0.90 |
| New Mask 15 | | 0.75 | | 0.48 | | 0.52 | | 0.65 | | 0.95 |
| New Mask 9 | | 0.90 | | 1.05 | | 0.65 | | 0.75 | | 0.90 |

The invention claimed is:

1. A patient interface assembly adapted to be connected to a gas supply pump to deliver pressurized breathable gas to a patient, comprising:
a patient interface in the form of a nasal-only mask or nasal prongs adapted to seal with the patient's nostrils to provide pressurized gas to the patient in the range of about 5-20 cmH$_2$O for the administration of CPAP therapy, the patient interface including an aperture;
one and only one supply tube connected to the patient interface, said supply tube being flexible along at least a part thereof and having a first end portion connected to the aperture of the patient interface and a second end portion connected to a swivel connector, the first end portion having an internal diameter ranging between about 9-15 mm; and
at least one strap structured to hold the patient interface in position on the patient's head, the at least one strap adapted to pass around the rear of the patient's head,
wherein the swivel connector includes a bore that is substantially larger than the diameter of the one and only one supply tube to connect to a gas delivery tube having an internal diameter of about 20 mm, whereby, in use, pressure swings that would otherwise result from a change in diameter are compensated for by controlling the pressure in the patient interface.

2. The patient interface assembly according to claim 1, wherein the first end portion of the supply tube has a first cross-sectional area, and the gas delivery tube has a second cross-sectional area, and the first cross-sectional area is at least about 50% to about 80% less than the second cross-sectional area.

3. The patient interface assembly according to claim 1, further comprising a sensor or transducer at or near the patient interface to generate a signal used to control the pressure in the patient interface.

4. A patient interface assembly adapted to be connected to a gas supply pump to deliver pressurized breathable gas to a patient, comprising:
a patient interface in the form of a nasal-only mask or nasal prongs adapted to seal with the patient's nostrils to provide pressurized gas to the patient in the range of about 5-20 cmH$_2$O for the administration of CPAP therapy, the patient interface including an a swivel elbow;
one and only one supply tube provided to the patient interface, the one and only one supply tube having a first end portion connected to the swivel elbow of the patient interface and a second end portion provided with a swivel connector, the first end portion having an internal diameter ranging between about 9-15 mm, said supply tube being flexible between the first and second end portions; and
a harness assembly structured to hold the patient interface in position on the patient's head, said harness assembly including a pair of upper straps positioned in use above the patient's ears and a pair of lower straps positioned in use below the patient's ears,
wherein the swivel connector includes a bore that is substantially larger than the diameter of the one and only one supply tube to connect to a gas delivery tube having an internal diameter of about 20 mm, whereby, in use, pressure swings that would otherwise result from a change in diameter are compensated for by controlling the pressure in the patient interface.

5. The patient interface assembly as claimed in claim 4, wherein the length of said supply tube is no more than about 17 cm.

6. The patient interface assembly as claimed in claim 5, wherein the internal diameter of the one and only one supply tube closest to the swivel elbow is relatively small compared to the remainder of the one and only one supply tube.

7. The patient interface assembly as claimed in claim 5, wherein the one and only one supply tube is coupled to the harness assembly to extend across the forehead and over the top of the patient's head in use.

8. The patient interface assembly according to claim 4, wherein the first end portion of the supply tube has a first cross-sectional area, and the gas delivery tube has a second cross-sectional area, and the first cross-sectional area is at least about 50% to about 80% less than the second cross-sectional area.

9. The patient interface assembly according to claim 4, further comprising a sensor or transducer at or near the patient interface to generate a signal used to control the pressure in the patient interface.

10. A patient interface assembly adapted to be connected to a gas supply pump to deliver pressurized breathable gas to a patient, comprising:
a patient interface in the form of a nasal-only mask or nasal prongs adapted to seal with the patient's nostrils to provide pressurized gas to the patient in the range of about 5-20 cmH$_2$O for the administration of CPAP therapy; and
a flexible supply tube in pressure communication with the patient interface,
wherein the patient interface includes an aperture to receive the entirety of the pressurized breathable gas supplied to the patient interface as a whole from the gas supply pump via the supply tube, said aperture defining a cross-sectional area that is less than a cross-sectional area of the supply tube at a position spaced away from or upstream of the patient interface, whereby, in use, pressure swings that would otherwise result from a change in cross-sectional area are compensated for by controlling the pressure in the patient interface.

11. The patient interface assembly as claimed in claim 10, wherein the supply tube consists of a single supply tube.

12. The patient interface assembly according to claim 10, wherein a cross-sectional area of said supply tube closest to the patient interface is at least about 50% to about 80% less than the cross-sectional area of the supply tube at a position spaced away from or upstream of the patient interface.

13. The patient interface assembly according to claim 10, further comprising a sensor or transducer at or near the patient interface to generate a signal used to control the pressure in the patient interface.

14. A patient interface assembly adapted to be connected to a gas supply pump to deliver pressurized breathable gas to a patient, comprising:
a patient interface in the form of a nasal-only mask or nasal prongs adapted to seal with the patient's nostrils to provide pressurized gas to the patient in the range of about 5-20 cmH$_2$O for the administration of CPAP therapy, the patient interface including an aperture; and
a flexible supply conduit provided in the vicinity of the patient's face having a first end portion connected to the aperture of the patient interface and a second end portion adapted to be in communication with the gas supply pump, the supply conduit having an internal diameter that reduces in size as gas is guided from the pump to the patient interface, whereby, in use, pressure swings that would otherwise result from a change in diameter are compensated for by controlling the pressure in the patient interface.

15. The patient interface assembly according to claim 14, wherein the supply conduit has a first diameter that receives gas from the pump and a second diameter in the vicinity to the patient interface for delivery of gas, said first diameter being greater than the second diameter.

16. The patient interface assembly according to claim 15, wherein the first diameter is about 20 mm, and the second diameter is about 9-15 mm.

17. The patient interface assembly according to claim 16, wherein beyond the vicinity of the patient's face the flexible supply conduit has the first diameter of about 20 mm.

18. The patient interface assembly according to claim 16, wherein the second diameter of about 9-15 mm is limited to a vicinity of the patient's face and head.

19. The patient interface assembly according to claim 16, wherein the second diameter of about 9-15 mm is limited to a vicinity of the patient's face.

20. The patient interface assembly according to claim 16, wherein the flexible supply conduit has a diameter of about 20 mm between the second end portion and the gas supply pump.

21. The patient interface assembly according to claim 14, wherein the patient interface includes only one said supply conduit.

22. The patient interface assembly according to claim 14, wherein a first cross-sectional area of the first end portion is at least about 50% to about 80% less than a second cross-sectional area of the second end portion.

23. The patient interface assembly according to claim 14, further comprising a sensor or transducer at or near the patient interface to generate a signal used to control the pressure in the patient interface.

24. A patient interface assembly adapted to be connected to a gas supply pump to deliver pressurized breathable gas to a patient, said gas pump being configured to deliver the gas via a standard 20 mm diameter air delivery tube, the patient interface assembly comprising:
a patient interface in the form of a nasal-only mask or nasal prongs adapted to seal with the patient's nostrils to provide pressurized gas to the patient in the range of about 5-20 cmH$_2$O for the administration of CPAP therapy, the patient interface including a swivel elbow;
one and only one supply tube providing communication of the gas between the air delivery tube and the patient interface, the supply tube having a first end portion connected to the swivel elbow of the patient interface and a second end portion connected to a swivel connector; and
at least one strap structured to hold the patient interface in position on the patient's head, the at least one strap adapted to pass around the rear of the patient's head,
wherein the supply tube includes a flexible reduced diameter portion relative to the air delivery tube as the gas is guided towards the patient interface in use, whereby, in use, pressure swings that would otherwise result from a change in diameter are compensated for by controlling the pressure in the patient interface.

25. The patient interface assembly according to claim 24, wherein the flexible reduced diameter portion is limited to a vicinity of the patient's face and head.

26. The patient interface assembly according to claim 24, wherein the flexible reduced diameter portion is limited to a vicinity of the patient's face.

27. The patient interface assembly according to claim 24, wherein the flexible reduced diameter portion of the supply tube has a cross-sectional area that is at least about 50% to about 80% less than a cross-sectional area of the air delivery tube.

28. The patient interface assembly according to claim 24, further comprising a sensor or transducer at or near the patient interface to generate a signal used to control the pressure in the patient interface.

29. A patient interface assembly adapted to be connected to a gas supply pump to deliver pressurized breathable gas to a patient, comprising:
a patient interface in the form of a nasal-only mask or nasal prongs adapted to seal with the patient's nostrils to provide pressurized gas to the patient in the range of about 5-20 cmH$_2$O for the administration of CPAP therapy, the patient interface including a swivel elbow;
a flexible supply tube in the vicinity of the patient's face having a first end portion connected to the swivel elbow of the patient interface and a second end portion provided with a swivel connector, the supply tube having an internal diameter of about 9-15 mm, wherein the internal diameter closest to the swivel elbow is relatively small compared to the remainder of the supply tube; and
at least one strap structured to hold the patient interface in position on the patient's head, whereby, in use, pressure swings that would otherwise result from a change in diameter are compensated for by controlling the pressure in the patient interface.

30. The patient interface assembly according to claim 29, wherein the relatively small diameter of the supply tube closest to the swivel elbow results in reduced discomfort to the patient if the patient rolls on the supply tube in use and/or results in a reduced obtrusiveness of the supply tube to the patient in use.

31. The patient interface assembly according to claim 29, wherein a cross-sectional area of the supply tube closest to the swivel elbow is at least about 50% to about 80% less than a cross-sectional area of the supply tube extending from the patient's head.

32. The patient interface assembly according to claim 29, further comprising a sensor or transducer at or near the patient interface to generate a signal used to control the pressure in the patient interface.

33. A patient interface assembly adapted to be connected to a gas supply pump to deliver pressurized breathable gas to a patient, comprising:
   a patient interface in the form of a nasal-only mask or nasal prongs adapted to seal with the patient's nostrils to provide pressurized gas to the patient for the administration of CPAP therapy, the patient interface being a soft membrane including an aperture;
   one and only one supply tube, said supply tube having a first end portion including an elbow connected to the aperture of the patient interface and a second end portion, an internal diameter of the one and only one supply tube closest to the patient interface being relatively small compared to the remainder of the one and only one supply tube, the supply tube being positioned in use to extend from the first end portion over a nose of the patient and between the patient's eyes to the second end portion positioned on top of the patient's head;
   a plurality of exit apertures through which breathable gas exits to atmosphere, the exit apertures being disposed adjacent to the connection of the first end portion of the supply tube and the patient interface;
   a swivel elbow connected to the second end portion of the supply tube, the swivel elbow having a first end portion connected to the second end portion of the supply tube and a second end portion for connecting to an air delivery tube in communication with the gas supply pump;
   at least one head strap structured to hold the patient interface in position on the patient's head, the at least one head strap adapted to pass around the rear of the patient's head and over the patient's ears in use; and
   a supply tube strap structured to hold the second end of the supply tube in position on top of the patient's head, the supply tube strap being positioned adjacent to the swivel elbow, wherein the relatively small portion of the one and only one supply tube closest to the patient interface is limited to a vicinity of the patient's face and head, whereby, in use, pressure swings that would otherwise result from a change in diameter are compensated for by controlling the pressure in the patient interface.

34. The patient interface assembly according to claim 33, wherein the first end portion has an internal diameter ranging between about 9-15 mm.

35. The patient interface assembly according to claim 34, wherein the second end portion of the swivel elbow on top of the patient's head has a diameter of about 20 mm.

36. The patient interface assembly according to claim 33, wherein at least a portion of the supply tube near the second end of the supply tube is flexible.

37. The patient interface assembly according to claim 33, wherein a portion of the supply tube extending from the first end portion and between the patient's eyes has a constant diameter.

38. The patient interface assembly according to claim 33, wherein the internal diameter of the one and only one supply tube closest to the patient interface is between about 9-15 mm.

39. The patient interface assembly according to claim 33, wherein the relatively small portion of the one and only one supply tube closest to the patient interface is limited to a vicinity of the patient's face.

40. The patient interface assembly according to claim 33, wherein a cross-sectional area of the supply tube closest to the patient interface is at least about 50% to about 80% less than a cross-sectional area of the remainder of the supply tube.

41. The patient interface assembly according to claim 33, wherein the relatively small internal diameter is limited to that portion of the supply tube between the first and second ends, and a diameter of the air delivery tube is about 20 mm from the second end of the supply tube to the gas supply pump.

42. The patient interface assembly according to claim 33, further comprising a sensor or transducer at or near the patient interface to generate a signal used to control the pressure in the patient interface.

43. A patient interface assembly adapted to be connected to a gas supply pump to deliver pressurized breathable gas to a patient, comprising:
   a frame;
   a patient interface mounted on the frame and including a pair of nasal prongs adapted to seal with the patient's nostrils to provide pressurized gas to the patient for the administration of CPAP therapy;
   one and only one supply tube, said supply tube being flexible and having a first end portion connected to the frame and a second end portion connected to a swivel connector, an internal diameter of the one and only one supply tube closest to the frame being relatively small compared to the remainder of the one and only one supply tube;
   a plurality of exit apertures in said frame through which breathable gas exits to atmosphere; and
   at least one head strap connected to the frame and structured to hold the patient interface in position on the patient's head, the at least one head strap adapted to pass over the patient's ears and over the top of the patient's head in use, whereby, in use, pressure swings that would otherwise result from a change in diameter are compensated for by controlling the pressure in the patient interface.

44. The patient interface assembly according to claim 43, further comprising a supply tube strap structured to hold the second end of the supply tube in position, the supply tube strap positioned on the supply tube at a position adjacent to the swivel connector.

45. The patient interface assembly according to claim 43, wherein the first end portion has an internal diameter ranging between about 9-15 mm.

46. The patient interface assembly according to claim 45, wherein the second end portion has a diameter of about 20 mm.

47. The patient interface assembly according to claim 43, wherein the supply tube has a length of about 17 cm.

48. The patient interface assembly according to claim 43, wherein the internal diameter of the one and only one supply tube closest to the patient interface is between about 9-15 mm.

49. The patient interface assembly according to claim 43, wherein the relatively small internal diameter of the one and only one supply tube closest to the frame is limited to a vicinity of the patient's face and head.

50. The patient interface assembly according to claim 43, wherein a cross-sectional area of the supply tube closest to the frame is at least about 50% to about 80% less than a cross-sectional area of the supply tube at the second end portion.

51. The patient interface assembly according to claim 43, further comprising a sensor or transducer at or near the patient interface to generate a signal used to control the pressure in the patient interface.

52. A patient interface assembly adapted to be connected to a gas supply pump to deliver pressurized breathable gas to a patient, comprising:
   a frame;
   a patient interface connected to the frame in the form of a nasal-only mask adapted to seal with the patient's nasal region to provide pressurized gas to the patient for the administration of CPAP therapy, the patient interface being a soft membrane;
   one and only one supply tube, said supply tube being flexible and having a first end portion connected to a swivel elbow provided to the frame, and a second end portion connected to a swivel connector, an internal diameter of the one and only one supply tube closest to the patient interface being relatively small compared to the remainder of the one and only one supply tube;
   at least one exit aperture in said supply tube through which breathable gas exits to atmosphere;
   a harness assembly structured to hold the patient interface in position on the patient's head, said harness assembly including a pair of upper straps positioned in use above the patient's ears, a pair of lower straps positioned in use below the patient's ears, and a central strap positioned on top of the patient's head in use; and
   a supply tube strap structured to hold the second end of the supply tube in position, the supply tube strap positioned on the supply tube at a position adjacent to the swivel connector, whereby, in use, pressure swings that would otherwise result from a change in diameter are compensated for by controlling the pressure in the patient interface.

53. The patient interface assembly according to claim 52, wherein the first end portion has an internal diameter ranging between about 9-15 mm.

54. The patient interface assembly according to claim 53, wherein the second end portion has a diameter of about 20 mm.

55. The patient interface assembly according to claim 52, wherein the internal diameter of the one and only one supply tube closest to the patient interface is between about 9-15 mm, said supply tube being dimensioned to extend at least partly across the patient's face and/or head.

56. The patient interface assembly according to claim 52, wherein the second end portion of the supply tube is attached to the central strap.

57. The patient interface assembly according to claim 56, wherein a small diameter portion of the supply tube extends from the first end portion and is dimensioned to extend between the patient's eyes in use.

58. The patient interface assembly according to claim 57, wherein the supply tube has a length of no more than about 17 cm.

59. The patient interface assembly according to claim 52, wherein the relatively small internal diameter of the one and only one supply tube closest to the frame is limited to a vicinity of the patient's face and head.

60. The patient interface assembly according to claim 52, wherein a cross-sectional area of the supply tube closest to the patient interface is at least about 50% to about 80% less than a cross-sectional area of the remainder of the supply tube.

61. The patient interface assembly according to claim 52, further comprising a sensor or transducer at or near the patient interface to generate a signal used to control the pressure in the patient interface.

* * * * *